United States Patent [19]

Weuthen et al.

[11] Patent Number: 5,500,155
[45] Date of Patent: Mar. 19, 1996

[54] DETERGENT MIXTURES OF FATTY ACID ISETHIONATE SALTS AND FATTY ALCOHOLS

[75] Inventors: Manfred Weuthen, Solingen; Karlheinz Hill, Erkrath; Manfred Biermann, Muelheim, all of Germany

[73] Assignee: Henkel Kommanditgesellschaft auf Aktien, Duesseldorf, Germany

[21] Appl. No.: 246,897

[22] Filed: May 13, 1994

[30] Foreign Application Priority Data

Mar. 18, 1994 [DE] Germany .............................. 44 09 321

[51] Int. Cl.$^6$ ............................ C11D 1/68; C11D 1/825; C11D 1/74; C11D 3/22
[52] U.S. Cl. ............. 252/557; 252/174.17; 252/174.18; 252/546; 252/548; 252/552; 252/554; 252/121; 252/153; 252/118; 252/DIG. 4; 252/174.24; 252/174.23; 252/134; 252/174; 252/DIG. 16; 252/DIG. 14; 252/545; 252/549; 252/174.19; 252/170; 252/171; 252/DIG. 1; 252/DIG. 2
[58] Field of Search ......................... 252/174.17, 174.18, 252/546, 548, 552, 557, 554, 121, 153, 118, DIG. 4, 174.24, 174.23, 134, 174, DIG. 16, DIG. 14, 545, 549, 174.19, 170, 171, DIG. 1, DIG. 2

[56] References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 3,687,855 | 8/1972 | Halpern | 252/106 |
| 3,951,842 | 4/1976 | Prince et al. | 252/134 X |
| 3,989,647 | 11/1976 | Prince | 252/535 |
| 4,007,125 | 2/1977 | Prince | 252/134 X |
| 4,100,097 | 7/1978 | O'Roark | 252/557 X |
| 4,169,074 | 9/1979 | Conrad et al. | 252/548 X |
| 4,180,470 | 12/1979 | Tokosh et al. | 252/134 X |
| 4,536,338 | 8/1985 | Urban et al. | 260/400 |
| 4,554,097 | 11/1985 | Schebece et al. | 252/134 X |
| 4,790,956 | 12/1988 | Weipert et al. | 252/557 X |
| 4,900,721 | 2/1990 | Bansemir et al. | 514/25 |
| 5,006,529 | 4/1991 | Resch | 514/721 |
| 5,100,573 | 3/1992 | Balzer | 252/134 X |
| 5,104,585 | 4/1992 | Fabry et al. | 252/554 X |
| 5,284,406 | 2/1994 | Scholz et al. | 252/546 X |
| 5,372,751 | 12/1994 | Rys-Cicciari et al. | 252/DIG. 16 |
| 5,374,716 | 12/1994 | Biermann et al. | 536/18.6 |
| 5,417,878 | 5/1995 | Takahata et al. | 252/DIG. 16 |
| 5,433,894 | 7/1995 | Massaro et al. | 252/DIG. 16 |

FOREIGN PATENT DOCUMENTS

| | | |
|---|---|---|
| 0176330 | 4/1986 | European Pat. Off. . |
| 0189332 | 7/1986 | European Pat. Off. . |
| 0249474 | 12/1987 | European Pat. Off. . |
| 0287300 | 10/1988 | European Pat. Off. . |
| 0285768 | 10/1988 | European Pat. Off. . |
| 0301298 | 2/1989 | European Pat. Off. . |
| 0409856 | 1/1991 | European Pat. Off. . |
| 0434460 | 6/1991 | European Pat. Off. . |
| 0441652 | 8/1991 | European Pat. Off. . |
| 457688 | 11/1991 | European Pat. Off. . |
| 0459769 | 12/1991 | European Pat. Off. . |
| 0472320 | 2/1992 | European Pat. Off. . |
| 0178131 | 2/1992 | European Pat. Off. . |
| 0542526 | 5/1993 | European Pat. Off. . |
| 2236727 | 2/1974 | Germany . |
| 2415927 | 10/1974 | Germany . |
| 2461139 | 7/1975 | Germany . |
| 2737739 | 3/1978 | Germany . |
| 2813324 | 10/1978 | Germany . |
| 2901070 | 7/1979 | Germany . |
| 2907792 | 9/1979 | Germany . |
| 9003977 | 4/1990 | WIPO . |
| 9113958 | 9/1991 | WIPO . |
| 9206158 | 4/1992 | WIPO . |
| 9206171 | 4/1992 | WIPO . |
| 9206157 | 4/1992 | WIPO . |
| 9206156 | 4/1992 | WIPO . |
| 9206153 | 4/1992 | WIPO . |
| 9206170 | 4/1992 | WIPO . |
| 9206164 | 4/1992 | WIPO . |
| 9206162 | 4/1992 | WIPO . |
| 9206161 | 4/1992 | WIPO . |
| 9206155 | 4/1992 | WIPO . |
| 9206154 | 4/1992 | WIPO . |
| 9206172 | 4/1992 | WIPO . |
| 9206152 | 4/1992 | WIPO . |
| 9206160 | 4/1992 | WIPO . |
| 9206159 | 4/1992 | WIPO . |
| 9206984 | 4/1992 | WIPO . |
| 9304161 | 3/1993 | WIPO . |
| 9306205 | 4/1993 | WIPO . |
| 9318130 | 9/1993 | WIPO . |

OTHER PUBLICATIONS

Happi, Sep., 56 (Sep. 1984).
Tens. Surf. Det. 25, 8 (1988).
"Kosmetische Faerbemittel", Verlag Chemie, Weinheim, 1984, pp. 81–106.
Chemical Abstracts, CA 79:93722, GB 1,315,461 (May 1973).
Chemical Abstracts, CA 77:136272, ZA 7,103,553 (Jan. 1972).

Primary Examiner—Douglas J. McGinty
Attorney, Agent, or Firm—Wayne C. Jaeschke; John E. Drach; Daniel S. Ortiz

[57] ABSTRACT

Detergent mixtures with improved processability contain 70 to 95% by weight of fatty acid isethionate salts, 5 to 30% by weight of fatty alcohols, 0 to 15% by weight of fatty acids, 0 to 15% by weight of alkyl and/or alkenyl oligoglycosides and 0 to 15% by weight of fatty acid N-alkyl polyhydroxyalkylamides, providing that the quantities add up to 100% by weight. The optionally self-emulsifying mixtures are suitable, for example, for the production of solid or liquid soaps.

8 Claims, No Drawings

DETERGENT MIXTURES OF FATTY ACID ISETHIONATE SALTS AND FATTY ALCOHOLS

BACKGROUND OF THE INVENTION

1. Field of the Invention

This invention relates to detergent mixtures containing fatty acid isethionate salts, fatty alcohols and optionally other surface-active ingredients and to liquid personal hygiene preparations of corresponding composition.

2. Description of the Related Art

Fatty acid isethionate salts (FIS) are anionic surfactants which have been known for some time.

By virtue of their high cleaning performance and their favorable skin-cosmetic compatibility, FIS can be used, for example, in bar soaps. A by no means complete overview on the use of fatty acid isethionates in conjunction with other ingredients is given in the following: DE-A 22 36 727. Toilet soap containing 40 to 85% of alkanesulfonates, 3 to 35% of fatty acids and 5 to 30% of fatty acid isethionates or taurides or alkylsulfates. DE-A 24 15 927. Bar soaps containing 30 to 60% of fatty acid isethionates, 2.5 to 25% of soaps and 3 to 25% of electrolyte salts (sodium sulfate, sodium chloride). DE-A 24 61 139. Bar soaps containing 3 to 70% of fatty acid isethionates and 3 to 20% of alkanesulfonates. DE-A 28 13 324. Bar soaps containing fatty acid isethionates and isethionic acid salts and, as processing aids, 2 to 6% of a substituted propanesulfonate. DE-A 29 01 070. Bar soaps containing 20 to 70% of fatty acid isethionates and 5 to 30% of sucrose fatty acid esters. DE-A 29 07 792. Bar soaps containing 20 to 70% of fatty acid isethionates and 30 to 50% of polysorbates. EP-A 0 176 330. Cleaning preparations preferably containing 55 to 98% of soap, 0.5 to 3% of isethionic acid salts and 5 to 45% of fatty acid isethionates. EP-A 0 178 131. A process for the production of bar soaps in which fatty acids and fatty acid isethionates are mixed under certain shear conditions. EP-A 0 189 332. A process for the production of bar soaps in which soap and fatty acid isethionates are mixed in the melt. EP-A 0 249 474. Cleaning preparations containing soap, fatty acid isethionates and antioxidants. EP-A 0 287 300. Cleaning preparations containing 20 to 80% of soap and 10 to 60% of fatty acid isethionates, alkanesulfonates, ethersulfates, alkylbenzenesulfonates, alkylsulfates, olefinsulfonates and/or fatty alcohol ethoxylates. EP-A 0 409 856. Non-foaming bar soaps containing 14 to 38% of fatty acid isethionates, alkylsulfates, alkylsulfonates, monoglyceride sulfates, alkylbenzenesulfonates and/or ethersulfates, 40 to 72% of water-insoluble emulsifiers, 0 to 25% of starch derivatives and 2 to 12% of water. EP-A 0 434 460. A solid detergent composition containing 15 to 35% of soap, 5 to 50% of fatty acid isethionates, 5 to 50% of water and 5 to 50% of organic solvents (methanol, ethanol and/or propanol). EP-A 0 441 652. Bar soaps containing fatty acid isethionates and sulfosuccinates in a ratio by weight of 10:1 to 2:1. EP-A 0 459 769. Cleaning preparations containing at least 25% of soap, 1 to 50% of fatty acid isethionates, 1 to 15% of fatty acids and 1 to 15% of sugar derivatives. EP 0 472 320. Solid skin cleansing preparations containing 20 to 70% of fatty acid isethionates and amphoteric surfactants of betaine structure in a ratio by weight of 10:1 to 2:1. EP-A 0 542 526. Mild cleaning preparations containing fatty acid isethionates, sulfosuccinates and amphoteric surfactants of betaine structure. WO 91/13958. A process for the production of syndet soaps in which an aqueous mixture of 30 to 80% of glycerol ethersulfonates and 5 to 30% of fatty acid isethionates is dried to a water content of 2 to 10% and then molded. WO 93/04161. Syndet soaps containing 40 to 90% of soap, 0.5 to 5% of cationic polymers, 0.5 to 10% of nonionic surfactants with an HLB value of 15 to 19.2 and 0.5 to 10% of fatty acid isethionates. WO 93/06205. Solid personal hygiene preparations containing 4 to 32% of alkylsulfates, fatty acid isethionates, sarcosinates and/or glycerol ethersulfonates, 4 to 30% of paraffin wax and other mild surfactants. WO 93/18130. Personal hygiene preparations in bar form containing 4 to 32% of alkylsulfates, fatty acid isethionates, sarcosinates and/or glycerol ether sulfonates, 4 to 30% of paraffin waxes, other mild surfactants and a mixture of zeolites. Fatty acid isethionates are generally produced and supplied in the form of compounds typically containing from 10 to 30% by weight of free fatty acids. Despite this generally unwanted impurity, products of the type in question have an unfavorably high melting point above 170° C. which seriously restricts their processability.

Now, the problem addressed by the present invention was to reduce the melting point of fatty acid isethionates by the addition of suitable co-surfactants to such an extent that products with an FIS content of at least 70% by weight which could be stirred or flaked at 100° C. would be obtained. Another problem addressed by the present invention was to select the type and quantity of co-surfactants in such a way that the performance properties of the resulting compounds would not be adversely affected. Finally, another problem addressed by the invention was to compound the fatty acid isethionates in such a way that the self-emulsifying systems would be obtained and would lead to stable aqueous emulsions and could also be used as liquid personal hygiene preparations.

DESCRIPTION OF THE INVENTION

The present invention relates to detergent mixtures containing: 70 to 95% by weight of fatty acid isethionate salts, 5 to 30% by weight of fatty alcohols, 0 to 15% by weight of fatty acids, 0 to 15% by weight of alkyl and/or alkenyl oligoglycosides and 0 to 15% by weight of fatty acid N-alkyl polyhydroxyalkylamides, with the proviso that the quantities add up to 100% by weight.

It has surprisingly been found that the addition of fatty alcohols to fatty acid isethionates not only reduces the melting point of the mixtures to below 100° C., it also enables surfactant compounds with excellent performance properties to be obtained. The mixtures are particularly suitable for the production of soaps.

Fatty acid isethionate salts

Fatty acid isethionates are known anionic surfactants which may be obtained by the relevant methods of preparative organic chemistry. They are normally produced by esterification of fatty acids with isethionic acid in the presence of alkaline catalysts. The fatty acid isethionates correspond to formula (I):

$$R^1CO\text{-}OCH_2CH_2SO_3X \qquad (I)$$

in which $R^1CO$ is an aliphatic, linear or branched, saturated or unsaturated acyl radical containing 6 to 22 carbon atoms and X is an alkali metal and/or alkaline earth metal, ammonium, alkylammonium, alkanolammonium or glucammonium.

Typical examples are fatty acid isethionates which are derived from caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof which are obtained, for example, in the pressure hydrolysis of natural fats and oils, in the reduction of aldehydes from Roelen's oxo synthesis or in the dimerization of unsaturated fatty acids.

Fatty acid isethionates derived from fatty acids containing 12 to 18 and, more particularly, 12 to 14 carbon atoms are preferably used in the form of their sodium and/or ammonium salts. The sodium or ammonium salt of coconut oil fatty acid isethionate is particularly preferred.

Fatty alcohols

Fatty alcohols are primary aliphatic alcohols corresponding to formula (II):

$$R^2OH \quad (II)$$

in which $R^2$ is an aliphatic, linear or branched hydrocarbon radical containing 6 to 22 carbon atoms and 0 and/or 1, 2 or 3 double bonds.

Typical examples are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol and erucyl alcohol and technical mixtures thereof which are obtained, for example, in the high-pressure hydrogenation of technical methyl esters based on fats and oils or aldehydes from Roelen's oxo synthesis and as monomer fraction in the dimerization of unsaturated fatty alcohols.

Technical fatty alcohols containing 12 to 18 carbon atoms, such as for example coconut oil, palm oil, palm kernel oil or tallow fatty alcohol, are preferred.

Fatty acids

In the context of the invention, fatty acids are aliphatic carboxylic acids corresponding to formula (III):

$$R^3CO\text{-}OH \quad (III)$$

in which $R^3CO$ is an aliphatic, linear or branched acyl radical containing 6 to 22 carbon atoms and 0 and/or 1, 2 or 3 double bonds.

Typical examples are caproic acid, caprylic acid, 2ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof which are obtained, for example, in the pressure hydrolysis of natural fats and oils, in the reduction of aldehydes from Roelen's oxo synthesis or in the dimerization of unsaturated fatty acids.

Technical fatty acids containing 12 to 18 carbon atoms, such as for example coconut oil, palm oil, palm kernel oil or tallow fatty acid, are preferred.

Alkyl and/or alkenyl oligoglycosides

Alkyl and/or alkenyl oligoglycosides correspond to formula (IV):

$$R^4O\text{-}[G]_p \quad (IV)$$

in which $R^4$ is an alkyl and/or alkenyl radical containing 4 to 22 carbon atoms, G is a sugar unit containing 5 or 6 carbon atoms and p is a number of 1 to 10. They are known substances which may be obtained by the relevant methods of preparative organic chemistry. EP-A1-0 301 298 and WO 90/03 977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index-p in general formula (IV) indicates the degree of oligomerization (DP degree), i.e., the distribution of mono- and oligoglycosides, and is a number of 1 to 10. Whereas p in a given compound must always be an integer and, above all, may assume a value p of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^4$ may be derived from primary alcohols containing 4 to 11 and preferably 8 to 10 carbon atoms. Typical examples are butanol, caproic alcohol, caprylic alcohol, capric alcohol and undecyl alcohol and technical mixtures thereof such as are obtained, for example, in the hydrogenation of technical fatty acid methyl esters or in the hydrogenation of aldehydes from Roelen's oxo synthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^4$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof which may be obtained as described above. Alkyl oligoglucosides based on hydrogenated $C_{12/14}$ coconut oil fatty alcohol having a DP of 1 to 3 are preferred.

Fatty acid N-alkyl polyhydroxyalkylamides

Fatty acid N-alkyl polyhydroxyalkylamides correspond to formula (V):

$$\begin{array}{c} R^6 \\ | \\ R^5CO\text{-}N\text{-}[Z] \end{array} \quad (V)$$

in which $R^5CO$ is an aliphatic acyl radical containing 6 to 22 carbon atoms, $R^6$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups.

The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (VI):

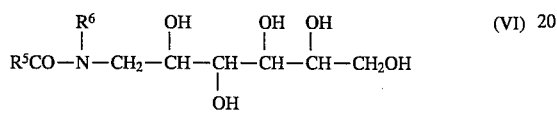

(VI)

Preferred fatty acid N-alkyl polyhydroxyalkylamides are glucamides corresponding to formula (VI) in which $R^6$ is hydrogen or an amine group and $R^5CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (VI) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

The use of fatty acid N-alkyl polyhydroxyalkylamides is also the subject of a number of publications. For example, their use as thickeners is known from European patent application EP-A1 0 285 768. FR-A 1 580 491 (Henkel) describes water-containing detergent mixtures based on sulfates and/or sulfonates, nonionic surfactants and optionally soaps which contain fatty acid N-alkyl glucamides as foam regulators.

International patent applications WO 92/6153; 6156; 6157; 6158; 6159 and 6160 relate to mixtures of fatty acid N-alkyl glucamides with anionic surfactants, surfactants of sulfate and/or sulfonate structure, ether carboxylic acids, ether sulfates, methyl ester sulfonates and nonionic surfactants. The use of these substances in various laundry detergents, dishwashing detergents and cleaning products is described in International patent applications WO 92/6152; 6154; 6155; 6161; 6162; 6164; 6170; 6171 and 6172.

Production of bar soaps

The detergent mixtures according to the invention are solid at normal temperature and soften gradually. At temperatures around 100° C., they are paste-like, but can readily be stirred or processed to flakes. Accordingly, their plastic behavior makes then particularly suitable for processing to bar soaps.

These solid bar soaps may be produced by any of the methods normally used for such products. The combination according to the invention of fatty acid isethionates, fatty acids and fatty alcohols above all provides for the formation of a compound with particularly good molding properties which becomes plastic on heating and which hardens on cooling, the molded products having a smooth surface. Typical processes for mixing or homogenizing, kneading, optionally milling, extrusion, optionally pelleting, extrusion, cutting, and bar-pressing are well known to the expert and may be used for the production of the bar soaps according to the invention. The production process preferably takes place at temperatures of 60 to 90° C., the meltable starting materials being introduced into a heatable kneader or mixer and the non-melting components being stirred in. For homogenization, the mixture may then be passed through a sieve before it is molded.

Industrial Applications

The detergent mixtures according to the invention are stirrable at 100° C. and may readily be processed to flakes. In addition, mixtures of fatty acid isethionates with fatty alcohols and alkyl oligoglycosides are self-emulsifying and form stable aqueous emulsions with an advantageously low viscosity. Accordingly, they are particularly suitable for the production of liquid personal hygiene preparations, such as liquid soaps for example.

Accordingly, the present invention relates to liquid personal hygiene preparations, preferably liquid soaps, containing 70 to 80% by weight of fatty acid isethionate salts, 15 to 20% by weight of fatty alcohols and 5 to 10% by weight of alkyl and/or alkenyl oligoglycosides with the proviso that the quantities shown add up to 100% by weight.

Auxiliaries and additives

Irrespective of whether the detergent mixtures are to be used as bar soaps or liquid products, they may contain the auxiliaries and additives typical of skin cleansing and skin-care preparations.

The typical auxiliaries and additives in question are, for example, oil components, emulsifiers, fats and waxes, thickeners, biogenic agents, film formers, fragrances, dyes, pearlescers, preservatives and pH regulators.

Suitable oil components are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{16-18}$ fatty alcohols, esters of linear $C_{10-18}$ fatty acids with branched alcohols, more particularly 2-ethylhexanol, esters of linear and/or branched fatty acids with dihydric alcohols and/or Guerbet alcohols, triglycerides based on $C_{6-10}$ fatty acids, vegetable oils, branched primary alcohols, substituted cyclohexanes and/or dialkyl ethers.

Suitable emulsifiers are both known w/o and o/w emulsifiers such as, for example, hydrogenated and ethoxylated castor oil, polyglycerol fatty acid esters or polyglycerol polyricinoleates. Typical examples of fats are glycerides; suitable waxes are inter alia beeswax, paraffin wax or microwaxes and also metal salts of fatty acids, such as magnesium stearate for example. Suitable thickeners are, for example, crosslinked polyacrylic acids and derivatives thereof, polysaccharides, more particularly xanthan gum, guar guar, agar agar, alginates and tyloses, carboxymethyl cellulose and hydroxyethyl cellulose; also fatty alcohols, monoglycerides and fatty acids, polyacrylates, polyvinyl alcohol and polyvinyl pyrrolidone. In the context of the invention, biogenic agents are, for example, plant extracts, protein hydrolyzates and vitamin complexes. Typical film formers are, for example, hydrocolloids, such as chitosan, microcrystalline chitosan or quaternized chitosan, polyvinyl pyrrolidone, vinyl pyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acids and fatty acid monoglycol esters. The dyes used may be any of the types suitable and authorized for cosmetic purposes, as listed for example in the publication entitled "Kosmetische Färbemittel" of the Farbstoffkommission der Deutschen Forschungsgemeinschaft, published by Verlag Chemie, Weinheim, 1984. These dyes are typically used in concentrations 0.001 to 0.1% by weight, based on the mixture as a whole.

The total percentage content of the auxiliaries and additives may be from 1 to 50% by weight and is preferably from 5 to 40% by weight, based on the particular preparation. The preparations may be produced in known manner, for example by hot emulsification, cold emulsification, hot-hot/ cold emulsification or PIT emulsification. These are all purely mechanical processes which do not involve any chemical reactions.

The following Examples are intended to illustrate the invention without limiting it in any way.

Examples

I. Surfactants used

1) Coconut oil fatty acid isethionate sodium salt (FIS)
2) Coconut oil fatty acid (FS)
3) Fatty alcohols (FA) $C_{12-18}$ Coconut oil fatty alcohol $C_{16/18}$ Tallow fatty alcohol Stearyl alcohol
4) $C_{12/16}$ Alkyl oligoglycoside (DP=1.3)

II. Performance tests

Mixtures of coconut oil fatty acid isethionate with the other constituents were introduced into a stirrer and heated to 100° C. Viscosity was visually evaluated. The results are set out in Table 1.

The Examples and Comparison Examples show that solutions with an isethionate content above 70% by weight which can be stirred and processed to flakes at 100° C. are obtained when fatty alcohols are used as additives. The results can be improved by using free fatty acids and/or alkyl oligoglucosides as further components.

TABLE 1

| | Viscosity of mixtures containing FIS at 100° C. | | | | | |
|---|---|---|---|---|---|---|
| Ex. | c(FIS) % | c(FS) % | FA | c(FA) % | c(APG) % | Viscos. |
| 1 | 74 | — | 16/18 | 26 | — | Liquid |
| 2 | 70 | 10 | 16/18 | 20 | — | Liquid |
| 3 | 74 | — | 12/18 | 16 | 10 | Liquid |
| 4 | 76 | — | 16/18 | 16 | 8 | Liquid |
| 5 | 76 | — | 18 | 15 | 9 | Liquid |
| C1 | 90 | 10 | — | — | — | Solid |
| C2 | 80 | 20 | — | — | — | Solid |
| C3 | 70 | 30 | — | — | — | Solid |

Legend:
c(FIS) = Concentration of fatty acid isethionate#
c(FS) = Concentration of fatty acid
c(FA) = Concentration fatty alcohol
c(APG) = Concentration of alkyl oligoglucoside
Viscos. = Viscosity

What is claimed is:

1. A detergent mixture consisting essentially of: (a) 70 to about 95% by weight of a fatty acid isethionate salt; (b) 5 to about 30% by weight of a fatty alcohol; (c) 0 to about 15% by weight of a fatty acid, (d) 0 to about 15% by weight of an alkyl oligoglycoside, an alkenyl oligoglycoside, or a combination thereof; (e) 0 to about 15% by weight of a fatty acid N-alkyl polyhydroxyalkylamide.

2. The detergent mixture of claim 1 wherein said fatty acid isethionate is a compound of the formula (I):

$$R^1CO\text{-}OCH_2CH_2SO_3X \qquad (I)$$

in which $R^1CO$ is an aliphatic, linear or branched, saturated or unsaturated acyl radical having 6 to about 22 carbon atoms and X is an cation selected from the group consisting of an alkali metal, alkaline earth metal, ammonium, alkylammonium, alkanolammonium, glucammonium and a combination thereof.

3. The detergent mixture of claim 1 wherein said fatty alcohol is a compound of the formula (II):

$$R^2OH \qquad (II)$$

wherein $R^2$ is an aliphatic, linear or branched hydrocarbon radical having 6 to about 22 carbon atoms and 0, 1, 2 or 3 double bonds.

4. The detergent mixture of claim 1 wherein said fatty acid is a compound of the formula (III):

$$R^3CO\text{-}OH \qquad (III)$$

wherein $R^3CO$ is an aliphatic, linear or branched acyl radical having 5 to about 22 carbon atoms and 0, 1, 2 or 3 double bonds.

5. The detergent mixture of claim 1 wherein said oligoglycoside is a compound of the formula (VI):

$$R^4O\text{-}[G]_p \qquad (IV)$$

wherein $R^4$ is an alkyl or alkenyl radical having 4 to about 22 carbon atoms, G is a sugar unit containing 5 or 6 carbon atoms and p is a number of 1 to 10.

6. The detergent mixture of claim 1 wherein said fatty acid N-alkyl polyhydroxyalkylamide is a compound of the formula (V):

$$R^5CO-N(R^6)-[Z] \qquad (V)$$

wherein $R^5CO$ is an aliphatic acyl radical having 6 to about 22 carbon atoms, $R^6$ is hydrogen, an alkyl or hydroxyalkyl radical having 1 to 4 carbon atoms and [Z] is a linear or branched polyhydroxyalkyl radical having 3 to 12 carbon atoms and 3 to 10 hydroxyl groups.

7. A self-emulsifying personal hygiene preparation consisting essentially of: (a) 70 to about 80% by weight of a fatty acid isethionate salt; (b) 10 to about 20% by weight of a fatty alcohol; (c) 5 to about 10% by weight of an alkyl oligoglycoside, an alkenyl oligoglycoside, or a combination thereof.

8. A self-emulsifying composition of claim 1.

* * * * *